(12) United States Patent
Trott

(10) Patent No.: US 9,174,900 B2
(45) Date of Patent: Nov. 3, 2015

(54) METHOD FOR PRODUCTION OF CO, $H_2$ AND METHANOL-SYNTHESIS GAS FROM A SYNTHESIS GAS, IN PARTICULAR FROM ACETYLENE OFF-GAS

(71) Applicant: LINDE AKTIENGESELLSCHAFT, Munich (DE)

(72) Inventor: Thomas Trott, Munich (DE)

(73) Assignee: LINDE AKTIENGESELLSCHAFT, Munich (DE)

( * ) Notice: Subject to any disclaimer, the term of this patent is extended or adjusted under 35 U.S.C. 154(b) by 0 days.

(21) Appl. No.: 14/403,203

(22) PCT Filed: May 8, 2013

(86) PCT No.: PCT/EP2013/001382
§ 371 (c)(1),
(2) Date: Nov. 24, 2014

(87) PCT Pub. No.: WO2013/174480
PCT Pub. Date: Nov. 28, 2013

(65) Prior Publication Data
US 2015/0152030 A1    Jun. 4, 2015

(30) Foreign Application Priority Data
May 24, 2012 (DE) .......................... 10 2012 010 312

(51) Int. Cl.
| | | |
|---|---|---|
| *C07C 29/151* | (2006.01) | |
| *C01B 3/12* | (2006.01) | |
| *C01B 3/50* | (2006.01) | |
| *C01B 3/52* | (2006.01) | |
| *C01B 3/56* | (2006.01) | |

(52) U.S. Cl.
CPC ................. *C07C 29/151* (2013.01); *C01B 3/12* (2013.01); *C01B 3/506* (2013.01); *C01B 3/52* (2013.01); *C01B 3/56* (2013.01); *C01B 2203/0283* (2013.01); *C01B 2203/0415* (2013.01); *C01B 2203/0435* (2013.01); *C01B 2203/0475* (2013.01); *C01B 2203/061* (2013.01); *C01B 2203/062* (2013.01); *C01B 2203/063* (2013.01); *C01B 2203/065* (2013.01); *C01B 2203/146* (2013.01); *Y02C 10/12* (2013.01)

(58) Field of Classification Search
CPC ............ C07C 29/151; C01B 3/12; C01B 3/52
See application file for complete search history.

(56) References Cited

U.S. PATENT DOCUMENTS

| | | | |
|---|---|---|---|
| 5,351,491 A | 10/1994 | Fabian | |
| 7,741,377 B2 * | 6/2010 | Van Den Berg et al. | 518/700 |
| 8,439,991 B2 * | 5/2013 | Abbott | 48/61 |
| 2011/0124749 A1 | 5/2011 | Abbott | |

FOREIGN PATENT DOCUMENTS

| | | |
|---|---|---|
| EP | 0563702 A2 | 10/1993 |
| EP | 1729077 A1 | 12/2006 |
| EP | 1918352 A1 | 5/2008 |
| EP | 1975123 A2 | 10/2008 |
| WO | 2009/019497 A2 | 2/2009 |

OTHER PUBLICATIONS

International Search Report dated Jul. 30, 2013 issued in corresponding PCT/EP2013/001382 application (pp. 1-3).

* cited by examiner

*Primary Examiner* — Sudhakar Katakam
(74) *Attorney, Agent, or Firm* — Millen, White, Zelano, Branigan, P.C.

(57) ABSTRACT

The invention relates to a method for production of a methanol-synthesis gas product stream (2), an $H_2$ product stream (3) and a CO product stream (4) from an $H_2$- and CO-containing synthesis gas stream (5).

23 Claims, 1 Drawing Sheet

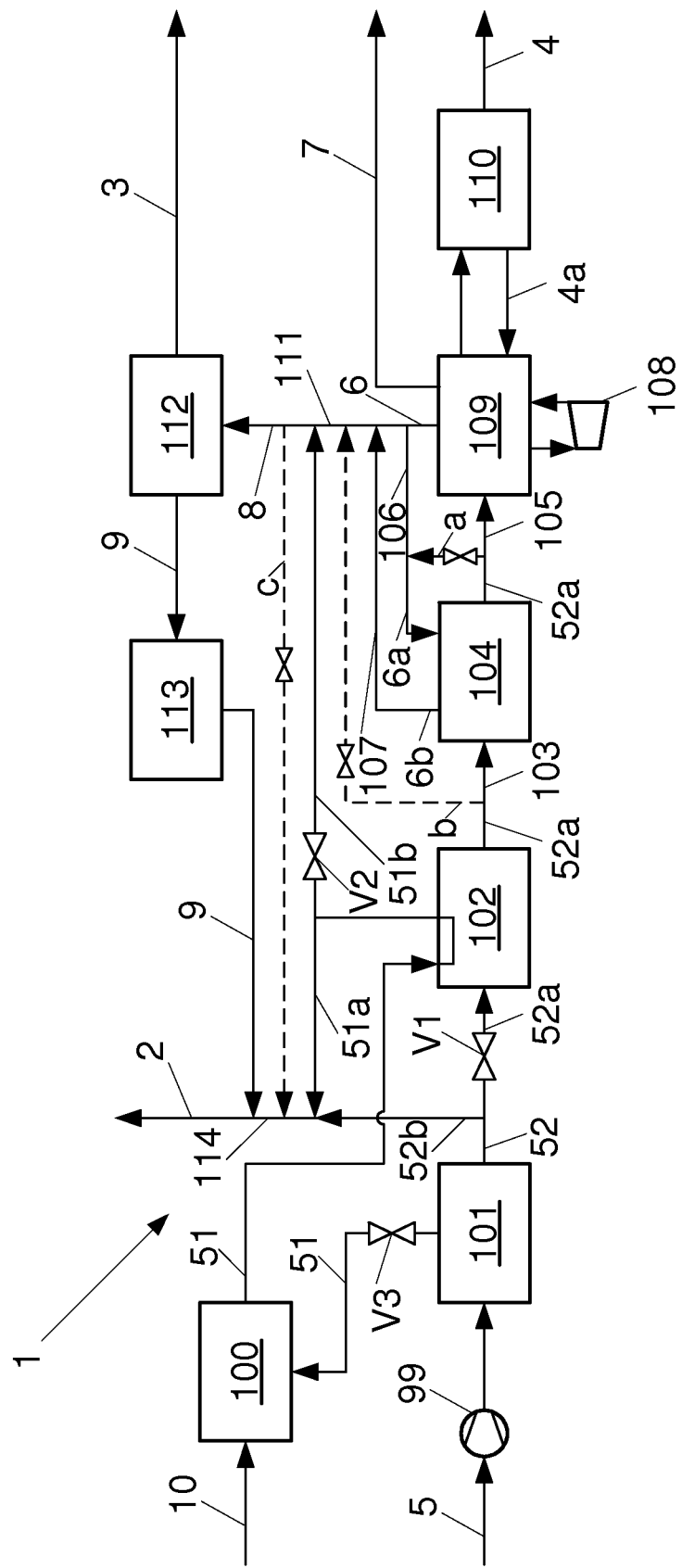

METHOD FOR PRODUCTION OF CO, H₂ AND METHANOL-SYNTHESIS GAS FROM A SYNTHESIS GAS, IN PARTICULAR FROM ACETYLENE OFF-GAS

The invention relates to a method for production of a methanol-synthesis gas, an $H_2$ product and a CO product from an $H_2$- and CO-containing synthesis gas, in particular an acetylene off-gas.

Methods for production of the abovementioned products from a synthesis gas are known from the prior art. In this case, however, it proves to be a challenge to produce the three said products in greatly fluctuating amounts in the context of a method as economical as possible from a possibly highly contaminated, $H_2$- and CO-containing synthesis gas.

This problem is solved by a method having the features of claim 1.

Accordingly, in the method according to the invention, a synthesis gas stream is provided which is divided into a first and a second synthesis gas substream, wherein only CO contained in the first synthesis gas substream is converted to $CO_2$ and $H_2$ (watergas-shift reaction) using steam admixed to the first synthesis gas substream, wherein the first converted synthesis gas substream and a part of the second unconverted synthesis gas substream are respectively fed to two separate scrubbing columns for scrubbing out $CO_2$ with an amine-containing scrubbing medium (e.g. MDEA), wherein, in particular, the scrubbing medium is regenerated in a shared column, wherein the methanol-synthesis gas product stream is mixed from one part of the scrubbed (converted) first synthesis gas substream and/or the other part (where present) of the (non-converted) second synthesis gas stream and also optionally two further streams (PSA residual gas and crude $H_2$ from a cold box, see below), in such a manner that a ratio of $(H_2-CO_2)/(CO+CO_2)$ that is required for the methanol synthesis is established, namely preferably in the range from 2.0 to 2.1, wherein, in addition, the (scrubbed) one part of the second synthesis gas substream is used for production of the CO product stream and the $H_2$ product stream, and wherein the other part (where present) of the scrubbed (converted) first synthesis gas substream is used for production of the $H_2$ product stream.

Preferably, the synthesis gas stream (feed gas) is compressed in a first process step in order to be able to achieve, in particular, the desired product pressures ($H_2$ and methanol syngas) without further compression. In addition, the effective gas volume, and therewith the dimensions of the plant components used can be reduced thereby. In addition, as a result, the steam used for the CO conversion need not be expanded excessively. In addition, a better absorption behaviour is achieved in the $CO_2$ scrubber, and subsequent cryogenic gas separation succeeds with a lower CO circulation rate, which reduces throughput and consumption at the CO compressor (compression of the CO product stream and of the CO circuit stream). Finally, owing to the compression provided at the outset of the feed in a pressure-swing adsorption (PSA), the $H_2$ yield is increased, and the residual gas amount that is to be compressed is thereby reduced.

Particularly preferably, as synthesis gas stream (feed stream), use is made of an acetylene off-gas that has been scarcely utilized to date for further production of valuable material, which acetylene off-gas usually occurs in large amounts as an inexpensive by-product during acetylene production.

A typical specification of such an off-gas (AOG) in mol % appears as follows:

| Constituent | mol % |
|---|---|
| $H_2$ | 59 to 64 |
| CO | 29 to 34 |
| $CO_2$ | 3.3 to 4.1 |
| $CH_4$ | 1.5 to 3.5 |
| $N_2$ + Ar + He | 0.3 to 1.0 |
| $O_2$ | 0.1 to 0.6 |
| $C_2H_6$ | 0.001 to 0.1 |
| $C_2H_4$ | 0.2 to 0.6 |
| $C_3H_4$ | 0.003 to 0.03 |
| Total S | <0.1 mg/(S.T.P.) m³ |
| NMP | Traces |
| Temperature | 15° C. to 40° C. |
| Pressure | 9 bar to 12 bar |

The method according to the invention is distinguished, in particular, by the possibility of effecting both the setting of the respectively required CO and $H_2$ product amounts and also—in relation thereto—the setting of the $(H_2-CO_2)/(CO+CO_2)$ ratio in the methanol-synthesis gas product stream which, for the methanol synthesis $(CO+2H_2 \leftrightarrow CH_3OH)$ is preferably in a range from 2.0 to 2.1.

The abovementioned setting can be performed, in particular, by appropriate portioning of the synthesis gas stream into the two synthesis gas substreams, and also apportioning thereof to the methanol-synthesis gas product stream that is to be produced and the hydrogen- and/or CO product stream that is to be produced.

For this purpose, e.g., for setting the CO product amount, the second (non-converted) synthesis gas substream can be fed to the said amine scrubber via a first valve in such a manner that, in the case of appropriate setting of the first valve, a part of the second synthesis gas substream passes through the said first valve into the amine scrubber, and is available for production of the CO product stream and/or $H_2$ product stream, and the other part is branched off upstream of the first valve and added to the methanol-synthesis gas product stream.

In addition, the converted (scrubbed) first synthesis gas substream, to set the $H_2$ product amount, can be added via a second valve to the pressure-swing adsorption unit (PSA) (see below) wherein, in the case of an appropriate position of the second valve, one part of the scrubbed first (converted) synthesis gas substream is branched off upstream of the second valve, and added to the methanol-synthesis gas product stream, and wherein the other part of the scrubbed first synthesis gas substream passes via the said second valve into the pressure-swing adsorption unit and is available for production of the $H_2$ product stream.

The $(H_2-CO_2)/(CO+CO_2)$ ratio being set in this case in the methanol-synthesis gas product stream is preferably measured (actual value), wherein the first synthesis gas substream is added via a third valve into the abovedescribed CO conversion, and the third valve is controlled in such a manner that the corresponding conversion of CO and $H_2O$ to $H_2$ and $CO_2$ controls the said ratio to the predefined reference value in the range from 2.0 to 2.1. If, e.g., the $H_2$ fraction is too low, the first synthesis gas substream is increased by corresponding adjustment of the third valve, in such a manner that per unit time more CO and $H_2O$ is converted to $H_2$ and $CO_2$. If the $H_2$ fraction is too large, the first synthesis gas substream is decreased by appropriate adjustment of the third valve.

In summary, the conversion, in the case of a preset CO product amount (first valve) is carried out in such a manner that, firstly, the desired $H_2$ product amount (second valve) results, and secondly the said ratio in the mixed methanol-synthesis gas product stream adopts a value in the range from 2.0 to 2.1 that is suitable for methanol synthesis.

In the event, that as feed, an acetylene off-gas stream is used, preferably, unsaturated hydrocarbons present therein, before the portioning of the synthesis gas stream, are hydrogenated in a catalytic purification unit to give saturated hydrocarbons, wherein, in particular, $C_2H_2$ and/or $C_2H_4$ is hydrogenated to form $C_2H_6$, or $C_3H_4$ and/or $C_3H_6$ is hydrogenated to form $O_3H_8$. In addition, preferably oxygen present in the acetylene off-gas stream is reacted with $H_2$ and CO that are likewise present therein to form $H_2O$ and $CO_2$. In addition, preferably, traces of sulphur and NMP (N-methylpyrrolidone) are retained from the acetylene off-gas stream in the abovementioned catalytic purification unit.

Preferably, the said one part of the second synthesis gas substream which serves, in particular, for production of the CO product or of the H2 product, after scrubbing out of $CO_2$, is subjected to a temperature-swing adsorption in a corresponding temperature-swing adsorption unit (adsorber station) for drying (removal of water) and for removing residual $CO_2$, wherein, preferably, at least one adsorber adsorbs, at low temperatures, $H_2O$ and $CO_2$ present in the said part of the second synthesis gas substream, and then the at least one adsorber loaded with the components is regenerated at comparatively high temperatures by purging with a crude hydrogen stream, wherein, as required, in particular in the partial-load case, a part of the part of the unconverted second synthesis gas substream that is dried by the said temperature-swing adsorption and is freed from $CO_2$ is admixed to the crude hydrogen stream.

The part of the unconverted second synthesis gas substream that is dried and freed from $CO_2$ in this manner is thereafter cryogenically separated (partial condensation or methane scrubbing) in a cold box at least into the CO product stream and a crude hydrogen stream, and also in particular a residual gas stream, wherein the CO product stream is compressed, and wherein at least one compressed substream of the CO product stream is used for generating the cold and/or heat (CO circuit streams) required for the said separation. For the production of cold, in this case, in particular a CO substream is expanded in a CO expander. The residual gas stream formed in the separation is preferably delivered at a battery limit and/or burnt.

In addition, the abovementioned crude hydrogen stream for the regenerating/purging the at least one adsorber of the temperature-swing adsorption unit is preferably split off from the crude hydrogen stream produced in the cold box and, after the regenerating/purging, is returned back to the crude hydrogen stream.

For generation of the $H_2$ product stream, then, preferably, the crude hydrogen stream and the other part of the scrubbed (converted) first synthesis gas substream are mixed to form a hydrogen-rich PSA feed stream which is subjected to a pressure-swing adsorption (PSA) for further purification. In this case, the PSA feed stream is passed under high pressure through at least one adsorber, wherein hydrogen present therein passes through the at least one adsorber and forms the $H_2$ product stream. The heavier components such as, e.g., CO, present in the PSA feed stream are adsorbed on the at least one adsorber. If the at least one adsorber is fully loaded, the adsorbed components are desorbed at lower pressure and the at least one adsorber is purged in particular with a purge gas formed from a substream of the $H_2$ product stream produced. A residual gas stream formed in this case containing the desorbed components and also the purge gas is then compressed and can be fed as a further component to the methanol-synthesis gas product stream.

As required, in particular with a predefinably small CO product stream and a comparatively large $H_2$ product stream, a part of the scrubbed part of the unconverted second synthesis gas substream can be admixed to the PSA feed stream. In addition, as required, in particular with a predefinably small $H_2$ product stream and a comparatively large CO product stream, a part of the crude hydrogen stream can be added to the methanol-synthesis gas product stream.

In addition, the problem according to the invention is solved by a plant for producing an $H_2$ product stream, a CO product stream and a methanol-synthesis gas product stream from an $H_2$- and CO-containing synthesis gas stream (e.g. acetylene off-gas).

The plant according to the invention preferably has a compressor which is designed to compress (see above) the synthesis gas stream (feed stream), wherein the compressor is preferably connected to a purification unit provided downstream of the compressor, which purification unit is designed for the catalytic hydrogenation of unsaturated hydrocarbons present in the (compressed) synthesis gas stream, and also for oxygen removal.

The said purification unit is preferably connected via a third valve to a watergas-shift reactor, in such a manner that a first synthesis gas substream is feedable via the third valve into the watergas-shift reactor which is designed for converting CO present in the first synthesis gas substream with $H_2O$ (steam) to $H_2$ and $CO_2$, wherein any conversion unit (watergas-shift reactor) in addition is connected to an amine scrubber unit which in turn is connected via a second valve to a crude hydrogen feed line for a pressure-swing absorption unit (PSA) and is also connected to an outlet line for the methanol-synthesis gas product stream, in such a manner that the first synthesis gas substream is feedable from the watergas-shift reactor into the amine scrubber unit and a part of the first synthesis gas substream is feedable into the crude hydrogen feed line of the PSA as a constituent of the methanol-synthesis gas product stream that is to be produced to the said outlet line and—according to setting of the second valve—the other part of the first synthesis gas substream via the second valve.

In addition, the purification unit is preferably connected via a first valve to the amine scrubber unit, in such a manner that a part of the second synthesis gas substream is feedable via the first valve into the amine scrubber unit, wherein, upstream of the first valve, the said outlet line branches off, in such a manner that—according to the setting of the first valve—the other part of the second synthesis gas stream is feedable into any outlet line as a further constituent of the methanol-synthesis gas product stream.

On the outlet line (MeOH syngas line)—after admixture of all substreams—preferably a sensor is provided for detecting the $(H_2\text{-}CO_2)/(CO+CO_2)$ ratio of the methanol-synthesis gas product stream mixed from the one part of the (converted) first synthesis gas substream, the other part of the (non-converted) second synthesis gas substream, and also optionally of the PSA residual gas and a part of the crude hydrogen from the cold box, wherein, for controlling the third valve, a control unit is provided which is designed to control any ratio (actual value) by corresponding adjustment of the third valve to a preset reference value (set value) in the range from 2.0 to 2.1 (see above).

The amine scrubber unit is preferably designed for the separate scrubbing of the converted first synthesis gas substream and also of the one part of the unconverted second synthesis gas substream, in order to remove or reduce $CO_2$ present therein, wherein the amine scrubber unit preferably has a shared column for regenerating the respectively used $CO_2$-loaded scrubbing medium, which shared column is designed for regenerating both scrubbing media. The amine scrubber unit is, in addition, connected via a first line to a temperature-swing adsorption unit for drying the scrubbed one part of the unconverted second synthesis gas substrate and for removing $CO_2$ still situated therein, wherein, in particular, the temperature-swing adsorption unit is designed to adsorb on at least one adsorber at low temperatures $H_2O$ and $CO_2$ present in the said part of the second synthesis gas substrate and then to regenerate the at least one adsorber loaded with the said components by purging with a crude hydrogen stream at comparatively high temperatures.

The temperature-swing adsorption unit is preferably connected via a second line to a cryogenic separation unit (cold box), in such a manner that the one part of the unconverted second synthesis gas substrate that has been dried and freed from $CO_2$ is feedable via any second line into the cold box which is designed to separate (see above) the part of the unconverted second synthesis gas substrate that has been dried and freed from $CO_2$ into the CO product stream that is to be produced, a crude hydrogen stream, and also, in particular, a residual gas stream. For compression of the CO product stream to the desired product pressure, the cold box is connected to a CO compressor, which is additionally designed to compress at least one CO substream for production of cold and/or heat to the desired CO circuit pressure (to approximately 30 bar to 40 bar) and to recirculate it to the cold box. In addition, the plant for production of the cold required for the cryogenic separation is equipped, in particular, to expand at least one of the abovementioned CO substreams of the CO circuit stream in a CO expander (to approximately 15 bar to 20 bar).

The cold box, in addition, is preferably connected via a regeneration/purge gas feed line to the temperature-swing adsorption unit which is designed for feeding in the crude hydrogen stream from the cold box which is used for the regeneration/purge into the temperature-swing adsorption unit. In addition, a first bridging line (bypass) that is equipped with a valve is provided which connects the second line to the regeneration/purge gas feed line upstream of the temperature-swing adsorption unit, in such a manner that, as required, in particular in the partial-load case, a part of the part of the second (non-converted) synthesis gas substrate that is dried and freed from $CO_2$ by the said temperature-swing adsorption can be admixed via the first bridging line to the crude hydrogen stream used for the regeneration/purge. In addition, a regeneration/purge gas return line is provided which connects the temperature-swing adsorption unit to the hydrogen feed line of the pressure-swing adsorption unit, in such a manner that loaded regeneration/purge gas (crude hydrogen stream) can be fed into the crude hydrogen feed line to the pressure-swing adsorption unit.

In addition, preferably, a second valve-equipped bridging line (bypass b) is provided which connects the first line (between the amine scrubber unit and the temperature-swing adsorption unit) to the crude hydrogen feed line of the pressure-swing adsorption unit, in such a manner that, as required, a part of the scrubbed part of the unconverted second synthesis gas substrate is feedable into the pressure-swing adsorption unit. In addition, a third valve-equipped bridging line (bypass) is provided which connects the crude hydrogen feed line of the pressure-swing adsorption unit to the said outlet line for the MeOH syngas, in such a manner that, as required, a PSA feed stream (crude hydrogen from the cold box, optionally converted and non-converted synthesis gas and also regeneration/purge gas from the TSA) that is conducted in the crude hydrogen feed line of the pressure-swing adsorption unit can be fed into the outlet line and thereby can be added to the methanol-synthesis gas product stream.

The pressure-swing adsorption unit is in detail preferably designed to deliver the (hydrogen-rich) PSA feed stream conducted in the crude hydrogen feed line at high pressure via at least one adsorber, wherein hydrogen passes through the at least one adsorber and forms the said $H_2$ product stream, and to adsorb on the at least one adsorber heavier components, in particular CO, present in this case in the PSA feed stream, wherein the pressure-swing adsorption unit is, in addition, designed to desorb at lower pressure the components that are adsorbed on at least one adsorber and, in particular, to purge them with a purge gas formed from a substream of the $H_2$ product stream generated. The pressure-swing adsorption unit is connected, in particular, to a residual gas compressor which, in turn, is connected to the said outlet line, in such a manner that a residual gas stream generated in the pressure-swing adsorption and containing the desorbed components and also the purge gas can be compressed in the residual gas compressor and then added to the methanol-synthesis gas stream.

BRIEF DESCRIPTION OF THE DRAWING

Further details and advantages of the invention are to be illustrated by the following FIGURE description of an exemplary embodiment based on the FIGURE.

In the drawing:

FIG. 1 shows a method according to the invention for producing an $H_2$-, CO- and methanol-synthesis gas product stream.

FIG. 1 shows a schematic diagram of a method and of a plant 1 for the production of an $H_2$ product stream 3, a CO product stream 4 and also of a methanol-synthesis gas product stream 2, which has a composition suitable for methanol synthesis. As synthesis gas 5 used, preferably what is termed an acetylene off-gas (AOG) 5 is used, which is a by-product of acetylene production which is available in comparatively large amounts.

The method according to the invention, however, is not restricted to AOG as feedstock, but can also be applied to other synthesis gases 5 of similar composition (especially similar $H_2$/CO ratio) with oxygen and/or unsaturated hydrocarbons for production of the three described products 2, 3, 4. The described process is also not restricted to the cited feed pressure according to the above table.

In a first process step, the synthesis gas stream (acetylene off-gas stream or AOG) 5 is first compressed 99 and then subjected in a purification unit 101 to a catalytic purification in which, in particular, in a 2-stage catalysis, the unsaturated hydrocarbons present in the synthesis gas stream 5 are hydrogenated ($C_2H_2$ and $C_2H_4$ to $C_2H_6$, or $C_3H_4$ and $C_3H_6$ to $O_3H_8$) and the oxygen present is reacted with $H_2$ or CO to form $H_2O$ or $CO_2$, respectively.

This prevents not only unsaturated hydrocarbons from freezing out in a subsequent cryogenic separation (cold box 109), but also the accumulation of explosive components such as $O_2$ and acetylene ($C_2H_2$) in all subsequent plant parts. In addition, preferably, traces of sulphur and NMP (N-methylpyrrolidone) are removed from the AOG 5.

After the above-described initial purification of the synthesis gas stream (AOG) 5, it is portioned into a first and a second synthesis gas substrate 51, 52, wherein the first (still warm) synthesis gas substrate 51, together with high-pressure steam 10 is fed to a water-gas shift reactor 100 in order to produce, by conversion of $CO+H_2O$ to form $CO_2+H_2$ at a predetermined amount of CO product (first valve V1) the required amount of $H_2$ product (second valve V2) and in order to set the $(H_2-CO_2)/(CO+CO_2)$ ratio necessary for the methanol synthesis in the range preferably 2.0 to 2.1 in the mixed methanol-synthesis gas product stream 2 (third valve V3).

In this case, in detail, the second synthesis gas substream 52 is fed via the first valve V1 to the CO2 scrubber unit (e.g. amine scrubber) 102, in such a manner that at an appropriate position of the first valve V1, one part 52a of the second (non-converted) synthesis gas substream 52 is fed via the said first valve V1 into the amine scrubber unit 102, wherein the other part 52b is added upstream of the first valve V1 to an outlet line 114 for the methanol-synthesis gas product stream 2.

The converted (scrubbed) first synthesis gas substream 51, to set the $H_2$ product amount, is added via a second valve V2 to a crude hydrogen feed line 111 of a pressure-swing adsorption unit (PSA) 112, wherein, at an appropriate position of the second valve V2, one part 51a of the scrubbed first (converted) synthesis gas substream 51 is branched off upstream of the second valve V2 into the said outlet line 114 and thereby added to the methanol-synthesis gas product stream 2, and wherein the other part 51b of the scrubbed, converted first synthesis gas substream 51 passes via the said second valve V2 into the crude hydrogen feed line 111 to the pressure-swing adsorption unit 112. The $(H_2-CO_2)/(CO+CO_2)$ ratio being established in the outlet line 114 in the methanol-synthesis gas product stream 2 is preferably continuously or repeatedly measured (actual value), wherein the said third valve V3, via which the first synthesis gas substream 51 is added into the watergas-shift reactor 100, is controlled in such a manner, via the conversion of CO and $H_2O$ to $H_2$ and $CO_2$ taking place in the watergas-shift reactor 100, the said ratio approaches the predefined reference value in the range from 2.0 to 2.1.

In the amine scrubber unit 102, a combined $CO_2$ removal is carried out (aMDEA scrubbing), wherein both the converted first synthesis gas stream (AOG stream) 51 and the said one part 52a of the unshifted second synthesis gas stream 52 are each fed to a scrubbing column for $CO_2$ reduction. Whereas the $CO_2$ in the converted $CO_2$-rich first synthesis gas stream 51 is preferably reduced to about 3 mol % $CO_2$ desired for the methanol synthesis, the $CO_2$ of the said part 52a of the unconverted second synthesis gas stream 52 is virtually completely removed down to a few mol ppm. In addition to the two scrubbing columns connected to one another energy efficiently on the scrubbing medium side, in particular, a shared regeneration of the scrubbing media of the two scrubbing columns can be carried out in only one regeneration column.

For the complete removal of the components water and $CO_2$, the part 52a of the unconverted second synthesis gas stream 52 is fed from the $CO_2$ scrubber 102 via a first feed line 103 into a temperature-swing adsorption unit (TSA) 104, before it passes via a second feed line 105 from the TSA 104 into a cryogenic gas separator which is carried out in a cold box 109. This prevents both these components from freezing out in the cold box 109 and also prevents any blockages of plate heat exchanger passages, product reduction and also product outage.

The loaded adsorber of the temperature-swing adsorption unit 104 is regenerated according to a defined step sequence (adsorber sequence) with a crude hydrogen stream 6a from the said cold box 109 at higher temperatures, before said adsorber is again available for adsorption. As required, e.g. in the partial-load case, one part of the dried part 52a of the unconverted second synthesis gas substream 52 which comes from the temperature-swing adsorption unit 104 is admixed to the crude hydrogen stream 6a used for the regeneration/purging, in order to provide the necessary regeneration gas amount, especially via a bypass or a first bridging line a which branches off from the second feed line 105.

For the synthesis gas stream (acetylene off-gas according to the table) 5 used that is defined at the outset, preferably a methane scrubbing 109 is carried out as a cryogenic gas separation process. At a lower $H_2/CO$ ratio and higher pressure in the synthesis gas stream (AOG) 5 used, however, a condensation process can also be used. The synthesis gas 52a in both processes is fractionated by rectification into the pure CO product stream 4, the crude hydrogen stream 6, and a residual gas stream 7.

In detail, in the methane scrubbing 109, first the part 52a of the second (non-converted) synthesis gas substream 52 (in particular in the form of a two-phase mixture) which is dried and freed from $CO_2$ is impinged in a methane scrubbing column with liquid methane, in such a manner that CO is scrubbed out of the ascending gaseous $H_2$— rich phase, wherein the crude hydrogen stream 6 is taken off at the top of the methane scrubbing column, which crude hydrogen stream 6 is passed (via the crude hydrogen feed line 111) into the pressure-swing adsorption plant 112. The condensate and the CO-loaded scrubbing methane, nitrogen, and still-dissolved hydrogen are taken off from the sump of the methane scrubbing column and passed to a second column, where $H_2$ with small amounts of CO that has been stripped off and also $N_2$ are taken off overhead as residual gas stream 7, and wherein the liquid phase occurring in the sump of the second column is passed into a third column from which methane is obtained as sump product which can be passed back into the methane scrubbing column and into the $H_2$ stripping column, wherein excess methane can be added to the residual gas stream 7. From the top of the third column, a fraction containing CO and $N_2$ is taken off, which fraction is added to a fourth column, from the top of which substantially $N_2$ which is added to the residual gas stream 7 is taken off and from the sump of which the CO product stream is taken off. Methane scrubbing methods which are designed differently are of course equally conceivable.

The CO thus produced is then compressed in a CO compressor 110 firstly to the product pressure or product pressures, secondly to the required CO circuit pressures. The CO circuit streams 4a are recirculated to the abovementioned low temperature process 109 and serve, e.g., as column heating, but they also deliver cold via expansion (Joule-Thomson effect) e.g. for overhead condensers. The majority of the cold requirement is generated by a CO expander 108 which expands a CO substream of the CO circuit stream 4a.

The crude hydrogen 6 generated in the cold box 109 is first mostly used as regeneration/purge gas (crude hydrogen stream 6a via purge gas feed line 106) in the temperature-swing adsorption unit (TSA) 104 and is then passed (via the regeneration/purge gas return line 107 and the crude hydrogen feed line 111) to the pressure-swing adsorption unit (PSA) 112 for fine purification.

The residual gas 7 from the cold box 109 is preferably delivered under low pressure at the battery limit and can, e.g., be underfired.

In order to produce the desired amount of hydrogen product, the crude hydrogen stream 6 from the cold box 109 and the other part 51b of the converted first synthesis gas stream 51 passed via the second valve V2 are passed to the PSA 112, where a high-purity $H_2$ product stream ($H_2$>99.9 mol %) is produced. As required, also a part of the scrubbed part 52a of the unconverted second synthesis gas substream 52 can also be fed to the PSA feed gas 8 (crude hydrogen feed line 111) via a second bridging line (bypass) b (in particular in the event of low CO and high $H_2$ amount of product) which bypass branches off from the first feed line 103 downstream of the amine scrubber unit 102 and upstream of the temperature-swing adsorption unit 104 and opens out into the crude hydrogen feed line 111.

Conversely, in particular in the case of low amount of $H_2$ product and high amount of CO product, a part of the crude hydrogen stream 6 from the cold box 109 can be run via a third bridging line (bypass) c directly into the methanol-synthesis gas product stream 2 (discharge line 114).

Accordingly, there are a minimum of one and a maximum of three sources for the $H_2$ production, namely crude hydrogen 6 from the cold box 109, converted synthesis gas 51*b* (via the second valve V2) and also non-converted synthesis gas 52*a* (via bypass b).

Since the residual gas 9 from the pressure-swing adsorption unit 112 principally contains $H_2$ and also CO, it is compressed in a residual gas compressor 113 to the desired pressure and forms one of a maximum of four components of the methanol-synthesis gas product stream 2. The further constituents are unconverted 52*b* and converted synthesis gas 51*a* and optionally crude hydrogen 6 (via bypass c). With the aid of the conversion, for various predetermined amounts of CO and H2 product, in each case the required $(H_2-CO_2)/(CO+CO_2)$ ratio from 2.0 to 2.1 in the methanol-synthesis gas product stream 2 can be set (third valve V3).

The method according to the invention, as a result, permits, in particular, the use of a feedstock gas (AOG) which has scarcely been utilized to date for further production of valuable material, is inexpensive and is available in large amounts as a by-product, for production of the high-quality grade products CO, $H_2$ and methanol syngas.

In this case, in particular via a suitable combination and control of the process groups (overall connection) both the amounts of CO and $H_2$ product and also the $(H_2-CO_2)/(CO+CO_2)$ ratio necessary for the methanol synthesis from 2.0 to 2.1 can be set. Thereby, maximum flexibility for the three products can be achieved, in dependence on the amount of AOG available, and maximum utilization of the AOG for these products is achieved, while only a small residual gas stream 7 is formed.

Finally, in particular, via a suitable interconnection of the process streams in only one $CO_2$ scrubber unit 102, both the unconverted 52*a* and also the converted AOG 51 can be treated, and the scrubbing medium can be regenerated in a single column.

| List of reference signs | |
|---|---|
| 1 | Plant |
| 2 | Methanol-synthesis gas product stream |
| 3 | H2 product stream |
| 4 | CO product stream |
| 4a | CO substream (circuit) |
| 5 | Feed (synthesis gas stream or AOG stream) |
| 6 | Crude hydrogen stream |
| 6a, 6b | Crude hydrogen stream (to/from TSA regeneration) |
| 7 | Residual gas stream from cold box |
| 8 | PSA feed stream |
| 9 | Residual gas stream (PSA) |
| 51 | First synthesis gas substream, converted |
| 51a | Part of the first synthesis gas substream |
| 51b | Other part of the synthesis gas substream |
| 52 | Second synthesis gas substream, unconverted |
| 52a | Part of the second synthesis gas substream (to/from CO2 scrubber) |
| 52b | Other part of the second synthesis gas substream (for the MeOH Syngas) |
| 99 | Feed compressor |
| 100 | Water-gas shift reactor |
| 101 | Purification unit for purifying the feed gas (e.g. catalytic hydrogenation) |
| 102 | CO2 scrubber (e.g. amine scrubber) |
| 103 | First feed line |
| 104 | Temperature-swing adsorption unit (TSA) |
| 105 | Second feed line |
| 106 | Regeneration/purge gas feed line |
| 107 | Regeneration/purge gas return line |
| 108 | CO expander |
| 109 | Methane scrubber unit (cold box) |
| 110 | CO compressor |
| 111 | Crude hydrogen feed line to PSA |
| 112 | Pressure-swing adsorption unit (PSA) |
| 113 | PSA residual gas compressor |
| 114 | Outlet line for methanol-synthesis gas product |
| V1, V2, V3 | Valves |
| a, b, c | Bridging lines (bypasses) |

The invention claimed is:

1. A method for production of a methanol-synthesis gas product stream (2) from an $H_2$- and CO-containing synthesis gas stream (5), said method comprising:
   portioning said $H_2$- and CO-containing synthesis gas stream (5) into a first and a second synthesis gas substream (51, 52), and converting (100) only CO contained in said first synthesis gas substream (51) to $CO_2$ and $H_2$ by using steam admixed to said first synthesis gas substream (51),
   scrubbing (102) the converted first synthesis gas substream (51) and a first part (52*a*) of said second synthesis gas substream (52), each in a separate column, with an amine-containing scrubbing medium to scrub out $CO_2$,
   forming said methanol-synthesis gas product stream (2) from a first part (51*a*) of the scrubbed converted first synthesis gas substream (51) and/or a second part (52*b*) of said second synthesis gas stream (52), in such a manner that a ratio of $(H_2-CO_2)/(CO+CO_2)$ that is required for the methanol synthesis is established in the methanol-synthesis gas product stream (2), wherein
   the scrubbed first part (52*a*) of said second synthesis gas substream (52) is further treated to produce a CO product stream (4) and a $H_2$ product stream (3), and wherein
   a second part (51*b*) of said scrubbed converted first synthesis gas substream (51) is further treated to produce said $H_2$ product stream (3).

2. The method according to claim 1, wherein said synthesis gas stream (5) is an acetylene off-gas stream produced in an acetylene plant.

3. The method according to claim 1, wherein said synthesis gas stream (5), before said portioning, is compressed (99).

4. The method according to claim 2, wherein unsaturated hydrocarbons are present in said synthesis gas stream (5), and said unsaturated hydrocarbons are catalytically hydrogenated (101) to form saturated hydrocarbons.

5. The method according to claim 1, wherein said first part (52*a*) of said second synthesis gas substream (52), after said scrubbing to scrub out $CO_2$, is subjected to a temperature-swing adsorption (104), wherein at least one adsorber adsorbs, at a low temperature, $H_2O$ and $CO_2$ present in said first part (52*a*) of said second synthesis gas substream (52), and said at least one adsorber, loaded with the adsorbed components, is regenerated at a higher temperature by purging with a crude hydrogen stream (6*a*).

6. The method according to claim 5, wherein, after said temperature-swing adsorption (104), said first part (52*a*) of said second synthesis gas substream (52) is separated in a cold box (109) into at least said CO product stream (4), a second crude hydrogen stream (6), and a residual gas stream (7), wherein said CO product stream (4) is compressed (110), and wherein at least one compressed substream (4*a*) of said CO product stream (4) is used for generating the cold and/or heat required for the said separation in said cold box (109).

7. The method according to claim 5, wherein said crude hydrogen stream (6*a*) for regenerating said at least one adsorber is a substream of said second crude hydrogen stream (6) from said cold box (109).

8. The method according to claim 6, wherein said second crude hydrogen stream (6) and said second part (51*b*) of the scrubbed converted first synthesis gas substream (51) are mixed to form a hydrogen-rich pressure swing adsorber feed stream (8) which is subjected to a pressure-swing adsorption (112) to produce said $H_2$ product stream (3), wherein hydrogen present in said pressure swing adsorber feed stream (8) is passed under high pressure through at least one adsorber of a pressure swing adsorber to form said $H_2$ product stream (3), and heavier components present in said pressure swing adsorber feed stream (8), are adsorbed on the at least one adsorber, and wherein the components that are adsorbed on at least one adsorber are desorbed at lower pressure.

9. The method according to claim 8, wherein a part of said scrubbed first part (52*a*) of said second synthesis gas substream (52) is admixed (b) with said pressure swing adsorber feed stream (8).

10. The method according to claim 8, wherein a part of said second crude hydrogen stream (6) is added (c) to said methanol-synthesis gas product stream (2).

11. The method according to claim 1, wherein said amine-containing scrubbing medium from said scrubbing of said first synthesis gas substream (51) and said scrubbing of said first part (52*a*) of said the second synthesis gas substream (52) is regenerated in a shared column.

12. The method according to claim 1, wherein the ratio of $(H_2-CO_2)/(CO+CO_2)$ established in said methanol-synthesis gas product stream (2) is in the range from 2.0 to 2.1.

13. The method according to claim 3, wherein said synthesis gas stream (5), before said portioning, is compressed (99) to a pressure in the range from 25 bar to 40 bar.

14. The method according to claim 4, wherein catalytic hydrogenation of said unsaturated hydrocarbons is performed after compression and before said partitioning of said synthesis gas stream (5).

15. The method according to claim 4, wherein said unsaturated hydrocarbons comprise (a) $C_2H_2$ and/or $C_2H_4$ and (b) $C_3H_4$ and/or $C_3H_6$, and wherein during the catalytic hydrogenation $C_2H_2$ and/or $C_2H_4$ are hydrogenated to form $C_2H_6$ and $C_3H_4$ and/or $C_3H_6$ are hydrogenated to form $C_3H_8$, and wherein said synthesis gas stream (5) further contains oxygen, $H_2$ and CO and, during said catalytic hydrogenation, oxygen is reacted with $H_2$ and CO to form $H_2O$ and $CO_2$.

16. The method according to claim 4, further comprising removing traces of sulphur and N-methylpyrrolidone from said synthesis gas stream (5).

17. The method according to claim 1, wherein said first part (52*a*) of said second synthesis gas substream (52), after said scrubbing to scrub out $CO_2$, is subjected to a temperature-swing adsorption (104).

18. The method according to claim 5, wherein in the case of a partial-load, a part of said first part (52*a*) of said second synthesis gas substream (52) that is removed from said temperature-swing adsorption (104) is admixed (a) with said crude hydrogen stream (6*a*).

19. The method according to claim 6, wherein said residual gas stream (7) is delivered at a battery limit and/or burnt.

20. The method according to claim 8, wherein the components adsorbed on said at least one adsorber of said pressure swing adsorber are desorbed at lower pressure and purged with a purge gas formed from a substream of said $H_2$ product stream (3) to form a residual gas stream (9) containing the desorbed components and the purge gas, and said residual gas (9) containing the desorbed components and the purge gas is compressed (113) and fed to the methanol-synthesis gas stream (2).

21. The method according to claim 8, wherein a CO product stream (4), a $H_2$ product stream (3), and a part of said scrubbed first part (52*a*) of said second synthesis gas substream (52) are admixed (b) with said pressure swing adsorber feed stream (8).

22. The method according to claim 8, wherein a $H_2$ product stream (3), a large CO product stream (4), and a part of said the crude hydrogen stream (6) are added (c) to said methanol-synthesis gas product stream (2).

23. A method for production of a methanol-synthesis gas product stream (2), an $H_2$ product stream (3) and a CO product stream (4) from an $H_2$- and CO-containing synthesis gas stream (5), said method comprising:

portioning said $H_2$- and CO-containing synthesis gas stream (5) into a first and a second synthesis gas substream (51, 52), and converting (100) only CO contained in said first synthesis gas substream (51) to $CO_2$ and $H_2$ by using steam admixed to said first synthesis gas substream (51), scrubbing (102) the converted first synthesis gas substream (51) and a first part (52*a*) of said second synthesis gas substream (52), each in a separate column, with an amine-containing scrubbing medium to scrub out $CO_2$, wherein said amine-containing scrubbing medium is regenerated in a shared column, forming said methanol-synthesis gas product stream (2) from a first part (51*a*) of the scrubbed converted first synthesis gas substream (51) and/or a second part (52*b*) of said second synthesis gas stream (52), in such a manner that a ratio of $(H_2-CO_2)/(CO+CO_2)$ that is required for the methanol synthesis is established in the methanol-synthesis gas product stream (2), wherein said ratio is in the range from 2.0 to 2.1, wherein the scrubbed first part (52*a*) of said second synthesis gas substream (52) is further treated in a temperature-swing adsorption unit (104) and a cryogenic gas separator (109) to produce a CO product stream (4) and a crude hydrogen stream (6), and a second part (51*b*) of said scrubbed converted first synthesis gas substream (51) and said crude hydrogen stream (6) are further treated in a pressure sing adsorber to produce said $H_2$ product stream (3).

\* \* \* \* \*